(12) United States Patent
Rosenberg et al.

(10) Patent No.: US 7,273,624 B2
(45) Date of Patent: Sep. 25, 2007

(54) STABLE DOSAGE FORMS CONTAINING UBIQUINONES

(75) Inventors: Joerg Rosenberg, Ellerstadt (DE); Joerg Breitenbach, Mannheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 649 days.

(21) Appl. No.: 10/380,009

(22) PCT Filed: Sep. 19, 2001

(86) PCT No.: PCT/EP01/10830

§ 371 (c)(1),
(2), (4) Date: Jun. 12, 2003

(87) PCT Pub. No.: WO02/24184

PCT Pub. Date: Mar. 28, 2002

(65) Prior Publication Data

US 2004/0014817 A1 Jan. 22, 2004

(30) Foreign Application Priority Data

Sep. 19, 2000 (DE) .............................. 100 46 541

(51) Int. Cl.
*A61K 9/14* (2006.01)
*A61K 9/20* (2006.01)
*A61K 9/26* (2006.01)
*A61K 9/48* (2006.01)
*B29B 9/00* (2006.01)

(52) U.S. Cl. ................ 424/489; 424/451; 424/464; 424/465; 424/469; 424/470; 264/5

(58) Field of Classification Search ................ None
See application file for complete search history.

(56) References Cited

U.S. PATENT DOCUMENTS

| 4,801,460 A | 1/1989 | Goertz et al. ................ 424/465 |
| 4,880,585 A | 11/1989 | Klimesch et al. ............ 264/141 |
| 5,785,976 A | 7/1998 | Westesen et al. ........... 424/400 |
| 5,834,472 A | 11/1998 | Sangekar et al. ........... 514/252 |
| 5,891,469 A * | 4/1999 | Amselem .................... 424/451 |
| 6,036,974 A * | 3/2000 | Tsushima et al. ........... 424/464 |
| 6,184,255 B1 * | 2/2001 | Mae et al. ................... 514/720 |
| 6,291,013 B1 * | 9/2001 | Gibson et al. ............ 427/213.3 |
| 6,806,069 B2 * | 10/2004 | Chokshi ...................... 435/170 |
| 7,026,361 B2 * | 4/2006 | Minemura et al. ............ 516/75 |

FOREIGN PATENT DOCUMENTS

| EP | 1464341 A1 * | 10/2004 |
| WO | WO86/04503 A1 * | 8/1986 |
| WO | 95/05164 | 2/1995 |
| WO | 98/08490 | 3/1998 |
| WO | 01/62226 | 8/2001 |

OTHER PUBLICATIONS

Database CA Online, Chem. Abst. Service, Accession No. 89:12171 (JP 52136912; Nov. 16, 1977).

* cited by examiner

*Primary Examiner*—S. Tran
(74) *Attorney, Agent, or Firm*—Novak Druce & Quigg, LLP

(57) ABSTRACT

The invention relates to stable solid dosage forms for peroral administration containing, in addition to an ubiquinone, at least one thermoplastically processible matrix-forming auxiliary agent.

13 Claims, No Drawings

STABLE DOSAGE FORMS CONTAINING UBIQUINONES

The present invention relates to stable dosage forms of ubiquinones for oral administration, comprising at least one melt-processable matrix-forming excipient, the ubiquinones being present as solid dispersion in the excipient matrix. In addition, a process for producing such forms has been found.

Ubiquinones are lipid-soluble substances with the basic structure of 2,3-dimethoxy-5-methyl-1,4-benzoquinone and an isoprenoid side chain with 1-10 dihydroisoprene units (n=1 to 10) of the general formula

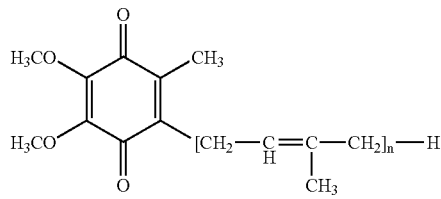

In particular, ubiquinones with n=3 to n=5 are relatively widespread in nature.

The present invention relates in particular to ubiquinone 50 (n=10), which is also referred to as coenzyme Q10. This is a substance with a yellow-orange color and a solidification point of about 50° C. which is readily soluble in organic solvents and fats but very slightly soluble in water.

Ubiquinones generally have very low solubility in water because of their structure, which causes problems in relation to adequate bioavailability.

In addition, the low melting point for example of ubiquinone 50 may cause difficulties in relation to processing and stability of dosage forms and limit the choice of a suitable form.

A basic requirement for satisfactory bioavailability is that the active ingredient is able to dissolve adequately in the aqueous medium in the digestive tract. Absorption of the active ingredient is possible only if it is present in dissolved form, because only dissolved active ingredients are able to cross the intestinal wall. In the case of slightly soluble active ingredients, this may lead to inadequate absorption and, associated therewith, low bioavailability.

There has been no lack of attempts to improve the bioavailability of slightly soluble active ingredients (cf. R. Voigt; "Pharmazeutische Technologie", Verlag Ullstein Mosby, 7$^{th}$ edition, 1993, pages 80-85). In particular, it has frequently proved to be advantageous for increasing the bioavailability to produce coevaporates or so-called solid dispersions in which the active ingredient can be in the form of a molecular dispersion in an excipient matrix. When the drug form dissolves in the body, the active ingredient can be released in molecular form from such solid dispersions directly and without expenditure of salvation energy.

However, the use of solid dispersions has a beneficial effect on the bioavailability of the active ingredient only if the active ingredient can also be absorbed quickly. If the absorption process is, however, slow, the active ingredient of low solubility recrystallizes in the aqueous medium in the intestinal lumen because a supersaturated solution of active ingredient may be produced on dissolution of the drug form. This is why the bioavailabilities achievable with solid dispersions are also unsatisfactory in certain cases.

Absorption of the active ingredient also often fails to be adequate because the active ingredient is released too slowly from the dosage form, for example tablet. Absorption into the blood circulation takes place for the great majority of active ingredients in the upper sections of the small intestine, i.e. relatively soon after passage through the stomach. Active ingredients which have not yet been adequately solubilized in this region of the small intestine can undergo only limited absorption.

To achieve optimal absorption rates it is therefore crucial, especially with slightly soluble active ingredients which crystallize readily, to achieve rapid and sufficiently long-lasting solubilization in the aqueous medium in the digestive tract without recrystallization occurring.

The addition of surface-active substances to formulations of slightly soluble active ingredients is generally known per se.

For example, U.S. Pat. No. 5,834,472 discloses that the bioavailability of an antifungal can be improved by also using a nonionic surface-active substance.

Since most surface-active substances are, however, liquid or semisolid at room temperature, to date there has mostly been production of oily liquid or semisolid preparations which are then introduced into hard or soft gelatin capsules. However, in the case of soft gelatin capsules there are often interactions between excipients and the gelatin shell of the capsule, leading to premature escape from the capsule.

Nor is use of surface-active substances in tablet formulations straightforwardly possible because the liquid or semisolid surface-active substances interfere with the compressibility in the conventional tabletting process, especially when the amounts of surface-active substances needed to solubilize the active ingredient are in the region of above 10% by weight.

WO 95/05164 describes the production of aqueous colloidal preparations of active ingredients with slight solubility in water, such as, for example, ubidecarenone, the active ingredients being present in the colloidal particles in the liquid state even below their melting point.

U.S. Pat. No. 5,785,976 discloses aqueous suspensions of colloidal solid lipid particles which may contain slightly soluble active ingredients, such as ubidecarenone, and which are obtained by emulsifying a melt of the active ingredients with an aqueous dispersing medium.

The production of pharmaceutical preparations by the melt extrusion process is known per se. Thus, for example, the process described in EP-A 240 904 or EP-A 240 906 makes it possible deliberately to control the properties of the formulations to be produced by a suitable choice or defined mixtures of the excipients employed.

It is an object of the present invention to find stable, solid presentations for oral use which, especially for the ubiquinones which have slight solubility in water, are capable of a rapid and, nevertheless, long-lasting solubilization after release (liberation) thereof from the dosage form.

We have found that this object is achieved by dosage forms which comprise a ubiquinone as active ingredient and a process for the production thereof.

As mentioned at the outset, suitable active ingredients are ubiquinones, especially ubiquinone 50. Slightly soluble ubiquinones in the sense of the invention are those in particular where at least 100 to 1000 parts, and preferably at least 10 000 parts, of water are necessary to dissolve 1 part of substance.

The dosage form may, besides the ubiquinone content, comprise further active ingredients, especially those with a ubiquinone-like action, e.g. other antioxidants, vitamins, as well as active ingredients of another type. A preferred embodiment of the present invention comprises single-drug products comprising as active-ingredient component at least a ubiquinone, especially ubiquinone 50.

The active ingredient component usually accounts for from 1 to 60% by weight, preferably 5 to 35% by weight and in particulars 8 to 30% by weight of the dosage form. Unless otherwise indicated, data in % by weight are based on the total weight of the dosage form.

The preparations of the invention comprise at least one melt-processable matrix excipient. Particularly suitable matrix-forming excipients are water-soluble, pharmaceutically acceptable polymers or sugar alcohols or mixtures thereof, as long as they melt without decomposition.

Matrix-forming excipients can in particular be selected from:

synthetic polymers such as polyvinyllactams, in particular polyvinylpyrrolidone (PVP); copolymers of vinyllactams such as N-vinylpyrrolidone, N-vinylpiperidone and N-vinyl-ε-caprolactam, but especially N-vinylpyrrolidone, with (meth)acrylic acid and/or (meth)acrylic esters, such as long-chain (meth)acrylates, e.g. stearyl (meth)acrylate, dialkylaminoalkyl (meth)acrylates, which may be quaternized, and maleic anhydride, vinyl esters, especially vinyl acetate, vinylformamide, vinylsulfonic acid or quaternized vinylimidazole; copolymers of vinyl acetate and crotonic acid; partially hydrolyzed polyvinyl acetate; polyvinyl alcohol; (meth)acrylic resins such as poly(hydroxyalkyl (meth)acrylates), poly(meth)acrylates, acrylate copolymers, e.g. from alkyl acrylates with (meth)acrylic acid, and copolymers of dimethylaminoethyl acrylates and-methacrylic esters (e.g. Eudragit types); polyalkylene glycols such as polypropylene glycols and polyethylene glycols, preferably with molecular weights above 1 000, particularly preferably above 2 000 and very particularly preferably above 4 000 (e.g. polyethylene glycol 6 000); polyalkylene oxides such as polypropylene oxides and, in particular polyethylene oxides, preferably of high molecular weight, especially with weight average molecular weights of more than 100 000; copolymers of methyl methacrylate and acrylic acid;

polyacrylamides, polyvinylformamide (where appropriate partially or completely hydrolyzed);

modified natural polymers, e.g. modified starches and modified celluloses, such as cellulose esters and, preferably cellulose ethers, e.g. methylcellulose and ethylcellulose, hydroxyalkylcelluloses, in particular hydroxypropylcellulose, hydroxyalkylakylcelluloses, in particular hydroxypropylmethylcellulose or hydroxypropyl-ethylcellulose, cellulose phthalates, in particular cellulose acetate phthalate and hydroxypropylmethylcellulose phthalate;

starch degradation products, in particular starch saccharification products, such as maltodextrin; and natural or predominantly natural polymers such as gelatin, polyhydroxyalkanoates, e.g. polyhydroxybutryric acid and polylactic acid, polyamino acids, e.g. polyhydroxybutyric acid and polyasparagine, polydioxanes and polypeptides, and mannans, especially galactomannans; and nonpolymeric binders such as polyols, for example those described in WO 98/22094 and EP 0 435 450, in particular sugar alcohols such as maltitol, mannitol, sorbitol, cellobiitol, lactitol, xylitol, erythritol and isomalt (Palatinit).

The polymers described above include for example the polyvinylpryyolidones having the proprietary name Kollidon® and weight average molecular weights of about 2 000 to about $1.5 \times 10^6$, for example the polyvinylpyrrolidone having the proprietary name Kollidon® 17 PF and a weight average molecular weight of about 7 000 to about 11 000; vinylpyrrolidone/vinyl acetate copolymers, in particular with vinylpyrrolidone:vinyl acetate ratio of from about 30:70 to about 60:30, for example the product having the proprietary name Kollidon® VA 64 and a vinlpyrrolidone:vinyl acetate ratio of about 60:40; hydroxayalkylcelluloses with 1 to 3 carbon atoms in the alkyl moiety, in particular hydroxypropylcellulose, for example the hydroxypropylcellulose having the proprietary name Klucel®; hydroxyalkylalkylcelluloses with 1 to 3 carbon atoms in the alkyl moieties, in particular hydroxypropylmethylcellulose (HPMC), for example the methylcellulose and methylcellulose derivative mixtures having the proprietary name Methocel® and containing ethyl, hydroxyethyl, hydroxypropyl and carboxymethyl ether groups, cellulose phthalates, especially hydroxypropylmethyl-cellulose phthalate, polyalkylene glycols with 2 and/or 3 carbon atoms in the alkylene moiety, especially polyethylene glycols, for example the polyethylene glycols having the proprietary name Lutrol® and weight average molecular weights of from 2 000 up to about 20 000, and polypropylene glycols, copolymers based on dimethylaminoethyl methacrylate and methacrylate and methacrylic esters such as methyl methacrylate and butyl methacrylate, for example the acrylic resins having the proprietary name Eudragit® E and based on dimethylaminoethyl methacrylate, methyl and butyl (methyl)acrylate with weight average molecular weights of about 150 000, copolymers with anionic characteristics based on methacrylic acid and methyl methacrylate, for example the acrylic resins having the proprietary names Eudragit® L and S and with weight average molecular weights of 250 000 to 135 000.

Pharmaceutically acceptable polymers are, in particular, homopolymers and copolymers of N-vinylpyrrolidone such as polyvinylpyrrolidone with Fikentscher K values of from 12 to 100, in particular K 17 to K 30, or copolymers with vinyl carboxylic esters such as vinyl acetate or vinyl propionate, particularly preferably copovidone (VP/VAc-60/40).

Also particularly suitable are polyvinyl alcohol or polyvinyl acetate, which may also be hydrolyzed or partially hydrolyzed, or acrylate polymers and the Eudragit type;

cellulose derivatives such as hydroxyalkycelluloses, for example hydroxypropylcellulose, or, in the case where slower release is desired, hydroxypropylmethylcelluloses which swell in water, for example hydroxypropylmethylcellulose (HPMC), preferably those with degrees of methoxy substitution in the region of 22% and degrees of hydroxypropoxy substitution in the region of 8%, particularly preferably HPMC types with viscosities of 4000 mPas, 15000 mPas or 10000 mPas, measured at 20° C. in 2% by weight aqueous solution. Also suitable are HPMC types with degrees of methoxy substitution in the region of 28 to 29% and degrees of hydroxypropoxy substitution in the region of 5 to 8.5%;

meltable sugar alcohols such as, for example, sorbitol, maltitol, isomalt, mannitol, xylitol, erythritol or mixtures thereof, maltitol, mannitol, xylitol and/or isomalt being preferred;

polyethylene glycols with molecular weights in the range from 1000 to 20000000 Dalton, preferably 4000 to 10000 Dalton.

The content of matrix-forming excipients in the dosage form is usually from 20 to 95% by weight, preferably 30 to 90% by weight and in particular 40 to 80% by weight.

Suitable and preferred surface-active substance are low molecular weight substances, i.e. nonpolymeric compounds, which have an HLB (hydrophilic lipophilic balance) of from 2 to 18 and are liquid at 20° C., or have a drop point in the range from above 20° C. to 50° C., preferably of up to 40° C. Preferred substances have an HLB of from 7 to 18, particularly preferably 10 to 15. The HLB system (hydrophilic-lipophilic balance system) assigns numerical values to surface-active substance; lipophilic substances receive low, and hydrophilic higher, HLB values (Fieldler, H. B., Lexikon der Hilfsstoffe für Pharmazie, Kosmetick und angrenzende Gebiete, 4th edition, Aulendorf: ECV Editio-Cantor-Verlag (1996)).

Examples of suitable surface-active substances are saturated and unsaturated polyglycolized glycerides, semisynthetic glycerides, fatty acid esters or ethers of fatty alcohols as long as they have the properties stated above. Oleic acid is also particularly suitable.

The term fatty acid refers to a group of aliphatic saturated or unsaturated carboxylic acids. The chains are usually unbranched and have 6 to 30, preferably 8 to 22, and in particular 8 to 18, carbon atoms. The saturated fatty acids include, for example, caproic acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid and melissic acid. The unsaturated fatty acids may be unsaturated one or more times, in particular unsaturated once, twice, three times, four times, five times or six times. Example of singly unsaturated fatty acids include palmitoleic acid, oleic acid and erucic acid, of doubly unsaturated fatty acids include sorbic acid and linolenic acid, of triply unsaturated fatty acids include linoleic acid and eleostearic acid, of quadruply unsaturated fatty acids include arachidonic acid, of quintuply unsaturated fatty acids include clupanodonic acid, and of sextuply unsaturated fatty acids include docosahexaenoic acid. Fatty acids for the purposes of the invention likewise include fatty acid derivatives such as hydroxylated fatty acids, e.g. hydroxystearic acid, dihydroxystearic acid and trihydroxystearic acid.

The term glycerides refers to esters of glycerol. Depending on the number of ester groups, reference is made to mono-, di- and triglycerides. The acid residue in a monoglyceride may be at position 1 or 2 and the acid residues of di- and triglycerides may be identical or different and be distributed in every conceivable way over the three possible positions of glycerol. The acid residues are preferably the fatty acids described above. Examples of monoglycerides include glycerol monobehenate, glycerol monocaprate, glycerol monococoate, glycerol monoerucate, glycerol monoisostearate, glycerol monolanolate, glycerol monolaurate, glycerol monolinoleate, glycerol monomyristate, glycerol monooleate, glycerol monopalmitate, glycerol monoricinoleate, glycerol monostearate, of the diglycerides include glycerol dicaprylate, glycerol dilaurate, glycerol dimyristate, glycerol dioleate, glycerol dipalmitate and glycerol distearate, of the triglycerides include glycerol tricaprylate, glycerol trilaurate, glycerol trimyristate, glycerol trioctanoate, glycerol trioleate, glycerol triricinoleate and glycerol tristearate.

The abovementioned fatty acid esters include in particular those of the formula II

(II)

where R is a straight-chain or branched, saturated or unsaturated, unhydroxylated, monohydroxylated, dihydroxylated or trihydroxylated aliphatic radical having 8 to 30 carbon atoms, the total of all x is zero to 100, y is 1 to 7, A is hydroxyl or $C_1$-$C_8$ alkoxy if y is 1 or A is derived from a polyol if y is 2 to 7.

The radical R is derived from fatty acid residues, for example those mentioned above, so that R is expediently a straight-chain or branched, in particular singly to doubly branched, saturated or unsaturated, in particular mono-, di- or triunsaturated, optionally mono-, di- or trihydroxylated aliphatic radical having 8 to 30, preferably 12 to 24 and in particular 10 to 24 carbon atoms. These include, in particular, palmityl, stearyl, arachidyl, hexadecenyl, oleyl, linolyl, linolenyl, ricinoleyl, eicosanyl and mono- and dihydroxystearyl, of which ricinoleyl and oleyl have particular significance.

If the nonionic surfactants of the formula (II) are ethoxylated, the total of all x gives the average ethoxylation number as, ordinarily, 3 to 100 and in particular 4 to 50.

If A is hydroxyl, then y is 1. Mention must be made in this context of, in particular, castor oil polyethoxylates and oleic acid polyethoxylates.

If A is optionally branched alkyloxy having 1 to 4, preferably 1 or 2, carbon atoms, then y is 1.

If A is derived from a polyol having 3 to 7 and in particular 6 carbon atoms, then the value of y=2 to 7 and preferably 3 to 6. Here, y hydroxyl hydrogen atoms of the radical A are replaced by in each case one radical R—CO—(EO)$_x$—, it being possible for two or more radicals R and two or more indices x to be identical or different. Preferably, two or more radicals R are identical, while the indices x may be different and, as a rule, follow a gaussian distribution. In particular, A is derived from a sugar alcohol, such as sorbitol or glycerol.

The corresponding sorbitan fatty acid esters or ethoxylated sorbitan fatty acid esters are particularly suitable, such as, for example, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (20) sorbitan tristearate, polyoxyethylene (20) sorbitan trioleate, polyoxyethylene (4) sorbitan monostearate, polyoxyethylene (4) sorbitan monolaurate or polyoxyethylene (4) sorbitan monooleate.

Also suitable are macrogol 6 cetylstearyl ether or macrogol 25 cetylstearyl ether.

Particular preference is given to polyoxyethylene glycerol ricinoleate 35, polyoxyethylene glycerol trihydroxystearate 40, PEG 660 12-hydroxystearate (polyglycol ester of 12-hydroxystearic acid (70 mol %) with 30 mol % ethylene glycol).

Particular preference is also given to vitamin E polyethylene glycol 1000 succinate (also known as vitamin E TPGS). Since this vitamin E derivative is also employed for food supplementation, the advantage of dosage forms which also-comprise vitamin E TPGS in addition to the ubiquinone active ingredient is that they make combination treatment possible.

The surface-active substances are present in the preparations in amounts of more than 1% by weight based on the total weight of the dosage form, and in particular the solid dispersion, i.e. the total amount of active ingredient, matrix-forming excipient and other excipients, and up to 40% by weight, preferably 2 to 25% by weight, and particularly preferably 20 to 25% by weight.

The preparations may also comprise conventional pharmaceutical excipients such as flavorings, antioxidants, silicas, release agents or dyes in the amounts usual therefor. The preparations preferably contain highly disperse silicas. It may also be advisable to add plasticizers, preferably triethyl citrate.

The preparations of the invention are produced by a melt process. The process is preferably carried out without addition of solvents.

The melt process is carried out in a kneader or a screw extruder. Examples of suitable kneaders are those supplied by Haake, Buss, List or Farrell.

The melt is preferably produced in a screw extruder, particularly preferably a twin-screw extruder with and without kneading disks or similar mixing elements. Corotating twin-screw extruders are particularly preferred.

Depending on the composition, the processing generally takes place at temperatures of from 40° C. to 150° C., preferably 50 to 120° C. The residue times are usually in the region of minutes.

The starting materials can be fed into the extruder or kneader singly or as a premix. They are preferably added in the form of powdered or granulated premixes. Thus, the liquid or oily surface-active substance can previously be mixed with another starting material to give free-flowing granules. Addition of the surface-active substance in liquid form, for example by liquid pumps, which are preferably heated in the case of semisolid substances, is likewise possible.

It is also possible first to dissolve the active ingredient in the surface-active substance, and then to granulate this mixture with the polymer. In this case, the active ingredient must not itself melt.

It may also be advisable first to melt the other starting materials and only then to add the active ingredient.

The starting materials are accordingly processed together to form a melt, which is processed by input of mechanical energy, in particular in the form of shear forces, to a homogeneous composition.

The homogeneous melt is then extruded through a die or a breaker plate and subjected to shaping. This can take place by pelletizing the extrudate by usual techniques, for example using rotating knives or compressed air, to result in pellets or granules. The shaping can also take place as described in EP-A 240 906 by the extrudate being passed between two counter-rotating calender rolls and being shaped directly to tablets. It is likewise possible to pass the melt through the open extruder head and, after solidification, to process it further where appropriate by grinding or by suitable granulation equipment such as roll mills or compacting units.

The solidified melts comprise the active ingredient preferably in the form of a molecular dispersion in the excipient matrix.

The dosage forms of the invention are also preferably solid. They may therefore be in particular powders, granules, pellets or tablets.

Granules or pellets can then be processed to tablets in conventional tablet presses. It is also possible for the preparations which have been initially obtained by calendering already in the form of mechanically stable tablets to be subjected to a grinding process and then to be compressed to tablets in a conventional way. If required, the tablets can then be provided with a conventional coating.

It is surprisingly possible according to the invention to obtain dosage forms, and especially tablets which, despite a high proportion of liquid or semisolid surface-active substances, are stable. In particular, they have good mechanical stability, i.e. especially dimensional stability, so that in particular they are not prone to be tacky or to soften. The forms are stable in storage at room temperature. This was not to be expected in view of the fact that not only the surface-active substances but also the ubiquinones are low-melting. Capsule filling can thus be dispensed with.

It was also not to be expected that terpenoid systems which additionally contain such a sensitive group as the quinone function can be processed virtually without decomposition even at temperature above the melting point.

The resulting dosage forms comprise the active ingredient embedded amorphously in particular. The preferred result is solid dispersions in which the active ingredient is in the form of a molecular dispersion. The dosage forms of the invention also make it possible for the ubiquinones of low solubility to be adequately solubilized and stably dispersed in aqueous medium. It was not to be expected that the dosage forms of the invention would be self-dispersing despite the highly lipid-like nature of the ubiquinones.

The term "molecular dispersion" is known to the skilled worker and essentially describes systems in which a substance, in the present case at least part and preferably the predominant part of the ubiquinone content, is homogeneously dispersed in a binder. In a molecular dispersion the system is free of interfaces. In such cases, the binder usually forms a matrix which, according to the invention, is formed by the binder component or at least by a predominant part of the binder component.

The content of active ingredient crystals in a formulation of the invention is usually below 12% and, in particular, below 5%. Statements concerning contents of crystals are based on the total amount of the active ingredient(s), in particular of the ubiquinone content.

A formulation of the invention which is essentially free of active ingredient crystals represents a particular embodiment of the present invention. The reduction in the crystal content means an increase in the homogenization of the active ingredient in the matrix.

Formulations of the invention in which there are essentially no crystalline contents of any constituent (essentially amorphous or crystal-free formulations) represent another particular embodiment of the present invention.

Known analytical methods can be used to investigate the state of such molecular dispersions, for example differential scanning calorimetry (DSC) or wide angle X-ray scattering measurements (WAXS measurements). The DSC analytical measurement of a molecular dispersion lacks the melting peak which occurs with the crystalline pure substance and is usually endothermic. Another possibility for identifying a molecular dispersion is the reduction in intensity and/or absence of typical X-ray diffraction signals in the WAXS analysis.

The preparations of the invention form, after dissolution in aqueous medium, in particular at pH 1, for at least one hour a stable solubilizate or a stable dispersion in which the active ingredient is preferably not in crystalline form.

The forms of the invention are suitable for use as food supplements, dietetic products and drug products.

General Method:

The surface-active substance and the matrix polymer were initially pregranulated by kneading the polymer in powder form with the liquid or semisolid surface-active substance to result in homogeneous, free-flowing granules. Then ubiquinone and highly disperse silica were admixed. This mixture was then metered through a weigh feeder into a melt-fed extruder. The extrusion process parameters were set so that the temperature of the melts was between 80 and 100° C. The emerging products were orange-colored melts which were more or less clear, depending on the excipient used, and which did not change in appearance even after cooling. Cooled pieces of melt dissolved in water at 37° C. to form opaque colloidal solutions.

| Example No. | 1 | 2 | 3 |
|---|---|---|---|
| Ubiquinone 50 | 20 | 20 | 20 |
| VA 64[1] | 67 | 67 | 67 |
| Cremophor RH40[3] | 12 | | |
| Vitamin E TPGS[3] | | 12 | |
| Oleic acid | | | 12 |
| Aerosil 200[4] | 1 | 1 | 1 |

[1] Copolymer of 60% by weight N-vinylpyrrolidone/40% by weight vinyl acetate
[2] Polyoxyethylene trihydroxystearate 40
[3] Vitamin E polyethylene glycol 1000 succinate
[4] Highly disperse silica, BET surface area 200 ± 25

We claim:

1. A process for producing a stable dosage form for oral administration, consisting essentially of:
   a.) providing a powdered or granulated premix comprising:
      (i) 5 to 35% by weight of at least one ubiquinone;
      (ii) 30 to 90% by weight of at least one melt-processable matrix-forming excipient selected from at least one of synthetic polymers, modified natural polymers, natural or predominantly natural polymers and sugar alcohols;
      (iii) 2 to 25% by weight of at least one surface-active substance with an HLB of from 2 to 18, which is liquid at 20° C. or has a drop point in the range from 20 to 50° C.; and optionally,
      (iv) other pharmaceutical excipients,
   b.) melting the premix, without addition of solvent, in a kneader or a screw-type extruder to obtain a homogeneous melt, and,
   c.) shaping and solidifying the melt to obtain a solid dispersion product.

2. The process as claimed in claim 1, wherein said matrix-forming excipient comprises at least one of water-soluble polymers, sugar alcohols and mixtures thereof.

3. The process as claimed in claim 1, wherein said matrix-forming excipient comprises a copolymer of N-vinylpyrrolidone.

4. The process as claimed in claim 1, wherein said surface-active substances have an HLB of from 10 to 15.

5. The process as claimed in claim 1, wherein said surface-active substances have a drop point in the range from 20 to 40° C.

6. The process as claimed in claim 1, wherein said surface-active substances comprise at least one of macrogol glycerol hydroxystearate, polyoxyethylene ricinoleate 35, and PEG 660 12-hydroxystearate.

7. The process as claimed in claim 1, wherein said surface-active substance comprises a vitamin E polyethylene glycol 1000 succinate.

8. The process as claimed in claim 1, wherein said active ingredient comprises ubiquinone 50.

9. The process as claimed in claim 1, wherein said melting the premix is carried out at a temperature of between 50-120° C.

10. The process as claimed in claim 1, wherein said melting the premix is carried out at a temperature of between 80-100° C.

11. The process as claimed in claim 1, wherein said sugar alcohol is a member selected from the group consisting of maltitol, mannitol, sorbitol, cellobitol, lactitol xylitol, erythritol, isomaly and mixtures thereof.

12. A process for producing a stable dosage form for oral administration, consisting essentially of:
   a.) providing a powdered or granulated premix comprising:
      (i) 5 to 35% by weight of at least one ubiquinone;
      (ii) 30 to 90% by weight of at least one melt-processable matrix-forming excipient selected from at least one of synthetic polymers, modified natural polymers, natural or predominantly natural polymers and sugar alcohols;
      (iii) 2 to 25% by weight of at least one surface-active substance with an HLB of from 2 to 18, which is liquid at 20° C. or has a drop point in the range from 20 to 50° C.; and optionally,
      (iv) other pharmaceutical excipients,
   b.) melting the premix, without addition of solvent, in a kneader or a screw-type extruder to obtain a homogeneous melt,
   c.) shaping and solidifying the melt to obtain a solid dispersion product, and
   d.) subsequently ground said solid dispersion product.

13. A process for producing a stable dosage form for oral administration, consisting essentially of:
   a.) providing a powdered or granulated premix comprising:
      (i) 5 to 35% by weight of at least one ubiquinone;
      (ii) 30 to 90% by weight of at least one melt-processable matrix-forming excipient selected from at least one of synthetic polymers, modified natural polymers, natural or predominantly natural polymers and sugar alcohols;
      (iii) 2 to 25% by weight of at least one surface-active substance with an HLB of from 2 to 18, which is liquid at 20° C. or has a drop point in the range from 20 to 50° C.; and optionally,
      (iv) other pharmaceutical excipients,
   b.) melting the premix, without addition of solvent, in a kneader or a screw-type extruder to obtain a homogeneous melt,
   c.) shaping and solidifying the melt to obtain a solid dispersion product, and
   d.) subsequently ground said solid dispersion product and compressed into tablet.

* * * * *